United States Patent [19]

Deinhammer et al.

[11] 4,017,613

[45] Apr. 12, 1977

[54] 2,4,4-TRICHLOROBUTADIENYL-1-PHOSPHATES AND PHOSPHONATES AND PESTICIDES MADE THEREFROM

[75] Inventors: Wolfgang Deinhammer, Munich; Marco Vulič, Freising; Manfred Wick, Munich; Helmut Prigge, Wolfratshausen-Farchet, all of Germany

[73] Assignee: Consortium fur Elektrochemische Industrie GmbH, Munich, Germany

[22] Filed: Oct. 20, 1975

[21] Appl. No.: 623,850

[30] Foreign Application Priority Data

Oct. 31, 1974 Germany .......................... 2451943

[52] U.S. Cl. ................................ 424/219; 260/957; 260/969

[51] Int. Cl.$^2$ ..................... A01N 9/36; C07F 9/09
[58] Field of Search ............ 260/957, 969; 424/219

[56] References Cited

FOREIGN PATENTS OR APPLICATIONS 1,298,519  7/1969  Germany .......................... 260/957

*Primary Examiner*—Anton H. Sutto
*Attorney, Agent, or Firm*—Allison C. Collard

[57] ABSTRACT

2,4,4-Trichlorobutadienyl-1-phosphate and 1-phosphonates are novel compounds, and are effective against organisms such as insects, acarides, and nematodes, and are suitable for application to plants.

21 Claims, No Drawings

2,4,4-TRICHLOROBUTADIENYL-1-PHOSPHATES AND PHOSPHONATES AND PESTICIDES MADE THEREFROM

The present invention relates to novel phosphoric acid and phosphonic acid esters, the process for their preparation, and their use as pesticides. The new class of compounds possesses improved pesticidal acvitity as compared with known phosphoric acid esters.

The compounds of the invention are classed as 2,4,4-trichlorobutadienyl phosphate or phosphonates, and have the general formula:

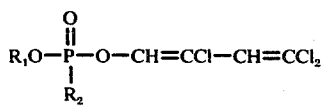

wherein $R_1$ is alkyl having 1 to 4 carbon atoms or alkenyl having 2 to 4 carbon atoms; $R_2$ is straight-chain alkyl having 1 to 4 carbon atoms, or phenyl.

These compounds contain two asymetrically substituted carbon atoms joined by a double bond, and they therefore exist in the following two stereoisomeric forms

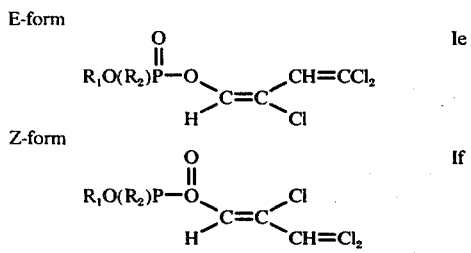

Both stereoisomers, as well as mixtures of the two stereoisomers, are included in the present invention.

In the above formulae, the radicals denoted by $R_1$ and $R_2$ may be identical or different in any given molecule.

The following individual compounds are particular examples of compounds of the above general formula I:

2,4,4-trichlorobutadienyl dimethyl phosphate (E-form and Z-form),
2,4,4-trichlorobutadienyl diethyl phosphate (E-form and Z-form),
2,4,4-trichlorobutadienyl diisopropyl phosphate (E-form),
2,4,4-trichlorobutadienyl diallyl phosphate (E-form),
2,4,4-trichlorobutadienyl methyl ethyl phosphate (E-form and Z-form),
2,4,4-trichlorobutadienyl methyl phenylpphosphonate (E-form), and
2,4,4-trichlorobutadienyl ethyl butylphosphonate (E-form and Z-form).

The compounds of the invention may be prepared by causing a compound of the general formula

in which $R_1$ and $R_2$ are defined as above, to react at a temperature of from 10° to 150° C, preferably from 40° to 100° C, with (a) 2,4,4,4-tetrachloro-but-2-enal or (b) 2,2,4,4-tetrachlorobut-3-enal.

These two alternative methods proceed stereoisomerically to a large extent: the use of (a) 2,4,4,4-tetrachlorobut-2-enal leads primarily to the E-form of the compounds of the invention, whereas the use of (b) 2,2,4,4-tetrachloro-but-3-enal leads to the Z-form. The reactions can be summarized by the following equations:

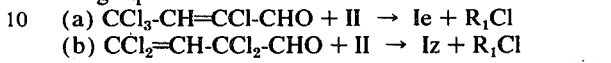

Both reactions (a) and (b) are exothermic, and it is therefore advantageous to carry out the process in an inert solvent, for example, an aliphatic or aromatic hydrocarbon or ether. One of the reactants may be first mixed with the solvent and then the other reactant added dropwise with stirring. The reaction proceeds almost quantitatively, and generally takes from 0.2 to 10 hours, depending on the reaction temperature. When the reaction is complete the solvent may be removed, and the oil remaining can be distilled in vacuo without appreciable decomposition.

2,4,4,4-tetrachloro-but-2-enal, used as a starting material, can be prepared in good yield from chloral and chloracetaldehyde by an aldol condensation. This may be carried out in the presence of a neutral or weakly basic aldol condensation agent, for example, piperidine acetate, ammonium acetate, or β-alanine, in an amount of from 1 to 20% by weight, preferably from 5 to 15% by weight, relative to the weight of the reactants. The reaction may be carried out at a temperature of from 50° to 150° C, preferably from 80° to 120° C. It is advantageously carried out in an inert solvent, for example, an aliphatic or aromatic hydrocarbon or chlorohydrocarbon. Water may be split off from the aldol condensation product by means of an acidic catalyst, for example, p-toluene sulphonic acid.

2,2,4,4-tetrachloro-but-3-enal may be prepared from 2,4,4,4-tetrachloro-but-2-enal by means of catalytic arrangement using a contact catalyst, c.f., Example 6.

The compounds of the invention have a pesticidal action, and are effective against organisms that suck the sap of and eat plants. They have, in particular, an insecticidal, acaricidal, and nematocidal action. They are effective not only against those organisms that are vulnerable to conventional phosphoric acid esters but also against those organisms that have become resistant to conventional phosphoric acid esters. They have an improved biocidal potency as compared with other phosphoric acid esters. The compounds have partly systemic properties, that is to say that they penetrate into the plant. They are effective against organisms when these organisms either come into contact with or eat the compounds.

The compounds may be used per se as pesticides or they may be formulated in conventional manner into, for example, solutions, emulsions, suspensions, powders, dusts, pastes, granulates, ULV-concentrates, and baits for the pests. Such formulations may be prepared in conventional manner by mixing the compound with a solid diluent and/or a liquid diluent, and, optionally, with a surfactant, for example, an emulsifier or dispersant, and a compound to stablize the formulation. The compounds of the invention may be used individually or two or more may be used in admixture with one another.

Suitable liquid diluents for use in the formulations are, for example, various aromatic liquids, e.g. benzene, toluene, xylene, and chlorobenzene; paraffins, e.g. various petroleum fractions; alcohols, e.g. butanol, glycol, and 2-ethylhexanol; ethers; esters; ketones, e.g. cyclohexanone; and strongly polar solvents, e.g. dimethylsulphoxide and dimethylformamide. Suitable solid diluents are, for examle, natural mineral powders, e.g. chalk, kaolin, talc, China clay, and aluminas; and synthetic mineral powders, e.g. silicates and highly dispersed silicic acids.

Any emulsifier present is suitably a non-ionic or anionic emulsifier, for example a polyoxyethylene fatty acid ester, a polyoxyethylene fatty alcohol ether, e.g. an alkylarylpolyglycol ether, or an alkylpolyglycol ether, an alkyl sulphonate, an aryl sulphonate, or an alkylbenzene sulphonate. Suitable dispersants that may be used are, for example, lignin, sulphite waste liquor, and methylcellulose.

The formulation may contain a compound to stablize the formulation, and this may be present in an amount of from 0.1 to 10% by weight, relative to the total weight of the formulation. Suitable compounds for this purpose are, for example, epoxy compounds, e.g. epichlorohydrin, octene-1-oxide, styrene oxide, and epoxydised soya bean oil; and acid anhydrides, e.g. acetic anhydride propionic anhydride, maleic anhydride, and phthalic anhydride.

Formulations in the form of granulates may contain granulate carriers, for example, pumice, brick chippings, crushed maize together with a binder (e.g. magnesium sulphate or gypsum hemilhydrate), bait material of animal origin (e.g. meatmeal and fishmeal), and bait material of plant origin (e.g. cornmeal).

Other additives may also be incorporated in the formulations, for example, nutritive substances for the crops, and pesticidally active substances, e.g. insecticides, acaricides, nematocide, fungicides, herbicides, and synergists (e.g. piperonyl-butoxide, and butylcarbitol, piperonylate.

The formulations may suitably contain from 0.1 to 95% by weight, preferably from 0.5 to 60% by weight, of the compounds of the invention. The formulations actually applied to the crops may suitably contain from 0.01 to 25% by weight, preferably from 0.03 to 5% by weight, of the compounds of the invention.

The formulations may be applied in any conventional manner, for example, by sprinkling, spraying, pouring, immersing, dusting, scattering, spreading, fumigating, disinfecting or feeding.

The compounds of the invention are advantageously applied in amounts of from 0.1 to 10 kg/ha, preferably from 0.3 to 5 kg/ha. These relatively small amounts of the compounds are generally adequate to control the pests, including those that have become resistant to other pesticides. The compounds of the invention thus have the advantage that, because they are used in relatively small amounts, they cause less pollution.

The following examples illustrate the invention. Examples 1 to 7 illustrate the manufacture of the compounds of the invention, and Examples 8 to 13 illustrate their pesticidal properties. Parts and percentages are by weight unless stated otherwise.

EXAMPLE 1

2,4,4-trichlorobutadienyl dimethyl phosphate (E-form)

240 g of a 41% solution of benzolic chloroacetaldehyde were added dropwise, while stirring, to 294 g of chloral and 10 g of piperidine acetate in 250 ml of benzene over a period of 30 minutes; the mixture was subsequently boiled for 3 hours in a water separator. The constituents volatile up to 50° C in a water jet vacuum were drawn off leaving 319g of a dark viscous oil. This was dissolved in 1.2 liters of xylene, reacted with 25 g of p-toluene sulphonic acid, and boiled in a water-separator until the water phase no longer distilled over. Xylene was then drawn off and the residue wad distilled at 0.2 to 0.4 torr. 132 g of a yellowish liquid distillate were obtained at 40° to 60° C; this consisted of up to 81% of 2,4,4,4-tetrachloro-but-2-enal, the remainder being xylene. The pure compound was obtained by fractional distillation. The boiling temperature, refractive index ($n_D^{20}$), and NMR-spectrum corresponded to data given in the literature.

5 g of this compound were dissolved in 25 ml of benzene and a solution of 3 g of trimethyl phosphite was added dropwise, while stirring, at a temperature of 75° C over a period of 10 minutes. The mixture was then boiled under reflux for 2 hours and the volatile constituents were removed at 12 torr. Finally, the mixture wad distilled at 0.02 torr. 4.2 g of a light yellow oil distillate were obtained at 96 to 98° C. It had the following NMR-spectral data: $\delta(CH_3O—)$ : 3.87 ppm, $j = 12$ Hz; $\delta(C=CH-C)$ : 6.75 ppm; $\delta(CH—O—P)$ : 6.97 ppm, $J = 6$ Hz.

EXAMPLE 2

2,4,4-trichlorobutadienyl-1-diethyl phosphate (E-form)

Over a period of 1 hour, 98 g of 80% aqueous chloroacetaldehyde were added dropwise, while stirring, and under reflux in a water-separator, to 443 g of chloral, 500 ml of perchorethylene and 20 g of ammonium acetate. The mixture was heated for a further 4 hours, and then cooled. The solution was filtered, reacted with 20 g of p-toluene sulphonic acid, and again boiled for 6 hours in a water-separator. After the perchlorethylene and excess chloral had been removed, the residue was distilled at 12 torr and 85° to 95° C. 146 g of a yellowish liquid were obtained consisting of up to 95% of 2,4,4,4-tetrachloro-but-2-enal (according to the NMR-spectrum). This product was purified by fractionated distillation.

7 g of the above product were dissolved in 30 ml of toluene and added to a solution of 7 g of triethyl phosphite in 50 ml of toluene, over a period of 3 minutes, while stirring, and a temperature of 60° C. The mixture was kept at a temperature of 80° C for another 2 hours, and then the volatile constituents were removed. Finally, distillation was carried out at 0.3 to 0.5 torr. 75 g of a light yellow oil distilled over at 108° to 111° C. It had the following NMR-spectral data: $\delta(CH_3)$ : 1.25 ppm, J = 7 Hz; $\delta(CH_2)$ : 3.85 – 4.35 ppm; $\delta(C=CH—O)$ : 6.58 ppm; $\delta(CH—O)$ : 6.82 ppm, $J = 6$ Hz.

EXAMPLE 3

2,4,4-trichlorobutadienyl-1-disiopropyl phosphate (E-form)

6 g of 2,4,4,4-tetrachloro-but-2-enal (prepared according to Example 2) were diluted with 30 ml of benzene and then added to a mixture of 30 ml of benzene and 7.3 g of triisopropyl phosphite, over a period of 10 minutes at 75° C, and the mixture was heated for 2 hours under reflux. After the benzene had been removed, the residue wad distilled at 0.3 torr. 6.8 g. of a light yellowish liquid distilled over at 125° to 128° C. It had the following NMR-spectral data: δ(CH₃) : 167 ppm, J = 6.5 Hz; δ(C̲H-CH₃) : 4.42 – 4.97 ppm; δ(C-CH=C) : 6.67 ppm; δ(=CH—O) : 6.9 ppm, J = 6 Hz.

EXAMPLE 4

2,4,4-trichlorobutadienyl-1-diallyl phosphate (E-form)

In a manner analogous to that described in Example 3, 4.1 g of product were obtained from 3 g of 2,4,4,4-tetrachloro-but-2-enal and 3.5 g of triallylphosphite. Boiling point : 142° – 145° C at 0.5 torr. NMR-spectral data: δ(CH₂O) : 4.5 – 4.7 ppm; δ(CH₂=) : 5.1 – 5.47 ppm; δ(CH₂=C̲H) : 5.65 – 6.27 ppm; δ(C-CH=CCl₂) : 6.57 ppm; δ(OCH=) : 6.8 ppm, J = 6 Hz.

EXAMPLE 5

2,4,4-trichlorobutadienyl-1-0-methyl phenylphosphonate (E-form)

In a manner analogous to that described in Example 3, 9.1 g of an oil which could not be distilled were obtained from 4.9 g of 2,4,4,4-tetrachloro-but-2-enal and 5 g of dimethyl phenylphosphonite. $n_D^{20}$ = 1.561. NMR-spectrum in CCl₄ : δ(OCH₃) : 3.77 ppm, J = 12 Hz; δ(Cl₂C=CH) : 6.53 ppm; δ(O-CH=) : 6.93 ppm. J = 13 Hz; δ(C₆H₅) : 7.2 – 8 ppm.

EXAMPLE 6

2,4,4-trichlorobutadienyl dimethyl phosphate (Z-form)

510 g of 2,4,4,4-tetrachloro-but-2-enal were heated with 260 g of silica gel for 15 hours at 110° C, and subsequently the reaction products were distilled off in a waterjet vacuum. The flask temperature was slowly raised to 200° C. 348 g of distillate were obtained which according to the NMR-spectrum, consisted of 62% of 2,2,4,4-tetrachloro-but-3-enal, 35% of 2,4,4,4-tetrachloro-but-2-enal, and 3% of other compounds. By fractional distillation, and at a pressure of 11 torr and a temperature of 73° to 74° C, pure 2,2,4,4-tetrachloro-but-3-enal were obtained. NMR-specrum: δ(CCl₂=CH) : 6.87 ppm; δ(CHO) : 9.35 ppm.

60 g of this 2,2,4,4-tetrachloro-but-3-enal in 100 ml of benzene were reacted with 45 g of trimethyl phosphite in 100 ml of benzene, while stirring, and at a temperature of 60 to 65° C over a period of 15 minutes, and subsequently heated under reflux for 1.5 hours. After the solvent had been removed, 81 g of crude product remained. This was distilled at 0.1 to 0.2 torr and yielded 65 g of product at 110 to 112° C. NMR-spectrum: δ(CH₃O—) : 3.9 ppm, J = 12 Hz; δ(C=CH-C) : 6.68 ppm; δ(CH-O-P) : 7.4 ppm, J = 6 Hz.

EXAMPLE 7

2,4,4-trichlorobutadienyl diethyl phosphate (Z-form)

184 g of 2,2,4,4-tetrachloro-but-3-enal (prepared in accordance with Example 6) were reacted in a manner analogous to that described in Example 6 with 166 g of triethyl phosphite, and 172 g of product were obtained by distillation at 0.2 to 0.3 torr and 121° to 125° C. NMR-spectrum : δ(CH₃) : 1.33 ppm, J = 7 Hz; δ(CH₂) : 3.95 – 4.47 ppm; δ(C=CH-C) : 6.67 ppm; δ(CH-O-P) : 7.33 ppm, J = 6 Hz.

EXAMPLES 8 to 13

The compounds of the general formula I prepared according to Examples 1 to 7 are summarized in the following Table 1. These compounds Nos. 1 to 7 were used as active substances for the biological tests described in Examples 8 to 13.

TABLE 1

| Compound/Example No. | R₁ | R₂ | Stereoisomeric Form |
|---|---|---|---|
| 1 | CH₃ | OCH₃ | E |
| 2 | C₂H₅ | OC₂H₅ | E |
| 3 | C₃H₇(iso) | —O—C₃H₇(iso) | E |
| 4 | CH₂CH=CH₂ | OCH₂CH=CH₂ | E |
| 5 | CH₃ | C₆H₅ | E |
| 6 | CH₃ | OCH₃ | Z |
| 7 | C₂H₅ | OC₂H₅ | Z |

Emulsion concentrates of each of the above active substances and of four comparative commercially available pesticides were prepared according to the following formulation:

Active substance — 20%
Cychlohexanone — 50%
Xylene — 20%
Emulsifier IHF — 10%

The "Emulsifier IHF" used is manufactured by Messrs. Hüls, Germany, and is a mixture of n-alkylbenzene sulphonates, alkylpolyglycol ethers and solvents. The four commercially available pesticides used were Gusathion H — 0-diethyl S-(4-oxo-3-H-1,2,3,-benzo-triazin-3-yl)-methyl dithiophosphate
Dimecron — 2-chloro-3-diethylamino-1-methyl-3-oxo-propenyl-dimethyl phosphate
Pantrin — N-methyl-1-naphthyl-carbonate
Drawinol — isopropyl [2-(1-methyl-n-propyl)-4, 6-dinitro-phenyl[ carbonate.

For each of Examples 8, 9, 11, 12 and 13, these emulsion concentrates were diluted with water to give spraying liquors of the desired concentration. (The concentrations specified in Tables 2 to 7 are the concentrations of active substances in ppm.)

For Example 10, the spraying liquors were prepared simply by diluting the active substances with acetone.

EXAMPLE 8

Aphis Test

Broad bean plants (*Vicia faba*) heavily infested with black bean aphids (*Aphis fabae*) were sprayed until dripping wet with the spraying liquors indicated in Table 2. The percentage death rates for the various spraying liquors were evaluated after 1 and 5 days and are given in Table 2. The results show that the compounds of the invention, and especially Compound No. 7, are more effective in lower concentrations than the comparative pesticide.

TABLE 2

| SPRAYING LIQUOR | | DEATH RATE (%) | |
|---|---|---|---|
| Compound No. | Concentration (ppm) | 1 Day | 5 Days |
| 1 | 125 | 99 | 100 |
|   | 62 | 97 | 100 |
|   | 31 | 95 | 97 |
| 2 | 125 | 100 | 100 |
|   | 62 | 100 | 100 |
|   | 31 | 96 | 100 |
| 3 | 62 | 93 | 100 |
|   | 31 | 87 | 73 |
|   | 16 | 78 | 53 |
| 4 | 62 | 97 | 100 |
|   | 31 | 84 | 99 |
|   | 16 | 64 | 88 |
| 5 | 62 | 100 | 100 |
|   | 31 | 94 | 99 |
|   | 16 | 82 | 84 |
| 6 | 31 | 99 | 97 |
|   | 16 | 95 | 82 |
|   | 8 | 65 | 71 |
| 7 | 31 | 100 | 98 |
|   | 16 | 96 | 93 |
|   | 8 | 84 | 69 |
| Gusathion H | 125 | 97 | 97 |
|   | 62 | 92 | 97 |
|   | 31 | 92 | 85 |

EXAMPLE 9

Planococcus Test

Germinated potatoes (*Solanum tuberosum*) were heavily infested with citrus louse (*Planococcus citri*) were sprayed until dripping wet, with the spraying liquors indicated in Table 3. The percentage death rate obtained with the various spraying liquors were evaluated after 1 and 6 days and are given in Table 3. The results show that the compounds of the invention are more effective in lower concentrations than the comparative pesticide Dimecron.

TABLE 3

| SPRAYING LIQUOR | | DEATH RATE (%) | |
|---|---|---|---|
| Compound No. | Concentration (ppm) | 1 Day | 5 Days |
| 2 | 250 | 85 | 91 |
|   | 125 | 75 | 89 |
|   | 62 | 73 | 83 |
| 6 | 500 | 100 | 96 |
|   | 250 | 97 | 92 |
|   | 125 | 86 | 78 |
|   | 62 | 80 | 75 |
|   | 31 | 77 | 69 |
| 7 | 250 | 91 | 100 |
|   | 125 | 84 | 87 |
|   | 62 | 59 | 92 |
|   | 31 | 41 | 84 |
| Dimecron | 1000 | 90 | 100 |
|   | 500 | 87 | 97 |
|   | 250 | 49 | 84 |
|   | 125 | 39 | 52 |

EXAMPLE 10

Calandra Test

The bottoms and lids of Petri dishes were sprayed with the acetonised solutions of active substances, both being sprayed with 1 ml. After the acetone had evaporated, the imagos of corn weevil (*Calandra granaria*) were placed in them. The spraying liquors used and the corresponding percentage death rates after 24 hours are listed in Table 4. It can be seen that the compounds of the invention have a better pesticidal effect, demonstrated by higher death rates in lower concentrations as compared with the comparative pesticides.

TABLE 4

| SPRAYING LIQUOR | | DEATH RATE (%) |
|---|---|---|
| Compound No. | Concentration (ppm) | After 24 Hours |
| 1 | 62 | 100 |
|   | 31 | 100 |
|   | 16 | 10 |
| 2 | 62 | 100 |
|   | 31 | 100 |
|   | 16 | 10 |
| 6 | 125 | 100 |
|   | 62 | 90 |
|   | 31 | 50 |
| 7 | 125 | 100 |
|   | 62 | 100 |
|   | 31 | 100 |
| Dimecron | 1000 | 100 |
|   | 500 | 30 |
|   | 250 | 0 |
| Gusathion H | 125 | 100 |
|   | 62 | 90 |
|   | 31 | 40 |

EXAMPLE 11

Epilachna Test

The bottoms of Petri dishes (diameter 10 cm, height 6 cm) were covered with filter paper and the larvae of the Mexican bean beetle (*Epilachna varivestis*) in the 2 – 3 phase were placed on it. The creatures were then soaked with 1 ml of spraying liquor as indicated in Table 5. They were sprayed again with 1 ml of spraying liquor after cut plants of the bush bean (*Phaseolus vulgaris*) had been placed in the dishes for the creatures to eat. The glass dishes were finally covered with lids which allowed air to reach the creatures. The percentage death rate after 24 hours are given in Table 5. It can be seen that the compounds of the invention are superior to the comparative pesticide Dimecron as regards their insecticidal effect on the larvae of the Mexican bean beetle.

TABLE 5

| SPRAYING LIQUOR | | DEATH RATE (%) |
|---|---|---|
| Compound No. | Concentration (ppm) | After 24 Hours |
| 2 | 250 | 100 |
|   | 125 | 100 |
|   | 62 | 80 |
|   | 31 | 50 |
| 7 | 250 | 100 |
|   | 125 | 100 |
|   | 62 | 100 |
|   | 31 | 90 |
| Dimecron | 500 | 100 |
|   | 250 | 100 |
|   | 125 | 70 |

EXAMPLE 12

Prodenia Test

This test was carried out analogously to the test of Example 1 except that *Prodenia litura* larvae in the 2 – 3 stage, and cut plant of the broad bean (*Vicia faba*) were used. The various spraying liquors and the percentage death rates after 48 hours are listed in Table 6. From the test results, it is apparent that the compound of the invention, in particular No. 7, are superior in their effect on the Prodenia larvae to the comparative substance Pantrin.

TABLE 6

| SPRAYING LIQUOR | | DEATH RATE (%) |
|---|---|---|
| Compound No. | Concentration (ppm) | After 48 Hours |
| 2 | 1000 | 100 |
|  | 500 | 70 |
|  | 250 | 0 |
| 6 | 500 | 100 |
|  | 250 | 90 |
|  | 125 | 50 |
| 7 | 125 | 100 |
|  | 62 | 100 |
|  | 31 | 70 |
| Pantrin | 1000 | 100 |
|  | 500 | 30 |

EXAMPLE 13

Acarina Test

Young apple trees infested with *Panonychus ulmi* were sprayed with the spraying liquors indicated in Table 6, until dripping wet. The percentage death rates after 2 days are listed in Table 7. It can be seen that the compounds of the invention are superior to the comparative pesticide Drawinol.

TABLE 7

| SPRAYING LIQUOR | | DEATH RATE (%) |
|---|---|---|
| Compound No. | Concentration (ppm) | After 2 Days |
| 6 | 250 | 93 |
|  | 125 | 77 |
| 7 | 250 | 96 |
|  | 125 | 83 |
| Drawinol | 250 | 72 |

What is claimed is:

1. A compound of the formula:

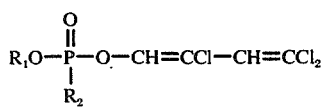

wherein $R_1$ is selected from the group consisting of alkyl having 1 to 4 carbon atoms and alkenyl having 2 to 4 carbon atoms; $R_2$ is selected from the group consisting of straight-chain alkyl having 1 to 4 carbon atoms, alkoxy having 1 to 4 carbon atoms, alkenyloxy having 2 to 4 carbon atoms, and phenyl.

2. A method of combating pests in a crop area which comprises applying to the crop area a compound as recited in claim 1 in an amount of from 0.1 to 10 kg/ha.

3. The method as recited in claim 2 wherein the said compound is applied in an amount of from 0.3 to 5 kg/ha.

4. 2,4,4-trichlorobutadienyl dimethyl phosphate in the E-form.

5. 2,4,4-trichlorobutadienyl dimethyl phosphate in the Z-form.

6. 2,4,4-trichlorobutadienyl diethyl phosphate in the E-form.

7. 2,4,4-trichlorobutadienyl diethyl phosphate in the Z-form.

8. 2,4,4-trichlorobutadienyl diisopropyl phosphate in the E-form.

9. 2,4,4-trichlorobutadienyl diallyl phosphate in the E-form.

10. 2,4,4-trichlorobutadienyl methyl ethyl phosphate in the E-form.

11. 2,4,4-trichlorobutadienyl methyl ethyl phosphate in the Z-form.

12. 2,4,4-trichlorobutadienyl methyl phenylphosphonate in the E-form.

13. 2,4,4-trichlorobutadienyl ethyl butylphosphonate in the E-form.

14. 2,4,4-trichlorobutadienyl ethyl butylphosphonate in the Z-form.

15. The process for the manufacture of a compound as recited in claim 1 which comprises reacting a compound of the formula

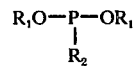

in which $R_1$ and $R_2$ are defined as in claim 1, at a temperature of from 10° to 150° C, with 2,4,4,4-tetrachloro-but-2-enal or with 2,2,4,4-tetrachloro-but-3-enal.

16. The process as recited in claim 15 wherein the reaction is carried out at a temperature of from 40° to 100° C.

17. The process as recited in claim 15 carried out in an inert solvent.

18. The process as recited in claim 17 wherein the solvent is selected from the group consisting of an aliphatic hydrocarbon, an aromatic hydrocarbon, an aliphatic ether and an aromatic ether.

19. A pesticide composition containing from about 0.1 to 95% by weight of a compound as recited in claim 1 as its active ingredient and a diluent.

20. A pesticide composition containing from 0.5 to 60% by weight of a compound as recited in claim 1 as its active ingredient and a diluent.

21. The pesticide composition as recited in claim 19 which is in the form of a member of the group consisting of a solution, emulsion, suspension, powder, dust, paste, granulate, concentrate and bait.

* * * * *